United States Patent [19]

Pumares et al.

[11] Patent Number: 5,797,842
[45] Date of Patent: Aug. 25, 1998

[54] STEERABLE ELECTROPHYSIOLOGY CATHETER

[75] Inventors: Fernando Pumares, San Bruno; Timothy McGrath, Milpitas, both of Calif.

[73] Assignee: E.P. Technologies, Inc., San Jose, Calif.

[21] Appl. No.: 740,621

[22] Filed: Oct. 31, 1996

[51] Int. Cl.⁶ .................................................. A61B 6/00
[52] U.S. Cl. ........................... 600/435; 604/95; 604/96; 604/280
[58] Field of Search ...................... 128/772, 652, 128/658; 604/280–283

[56] References Cited

U.S. PATENT DOCUMENTS 5,363,861  11/1994  Edwards et al. ................ 128/772
5,372,587  12/1994  Hammerslag et al. ........... 128/772

*Primary Examiner*—Max Hindenburg
*Assistant Examiner*—Pamela L. Wingood
*Attorney, Agent, or Firm*—Oppenheimer Wolff & Donnelly LLP

[57] ABSTRACT

A steerable catheter includes a handle, an elongated catheter body, a steering tube formed by an elongated coiled spring, the steering tube having a distal end that terminates short of the distal end of the catheter, and a steering spring having a bendable portion extending outside the distal end of the steering tube for bending the distal end of the catheter in response to an applied force exerted by one or more steering wires. A controller is positioned on the handle and attached to the steering wire, for applying tension. At least one and preferably two sleeves of polymeric material are heat shrunk around a part, but not all of the length of the distal portion of the catheter which extends distally from the elongated coiled spring. The bending characteristics of the catheter are modified by the length, and thickness of the sleeves as well as the physical characteristics of the polymer used. The preferred polymeric material is a polyester such as polyethylene terephthalate.

26 Claims, 4 Drawing Sheets

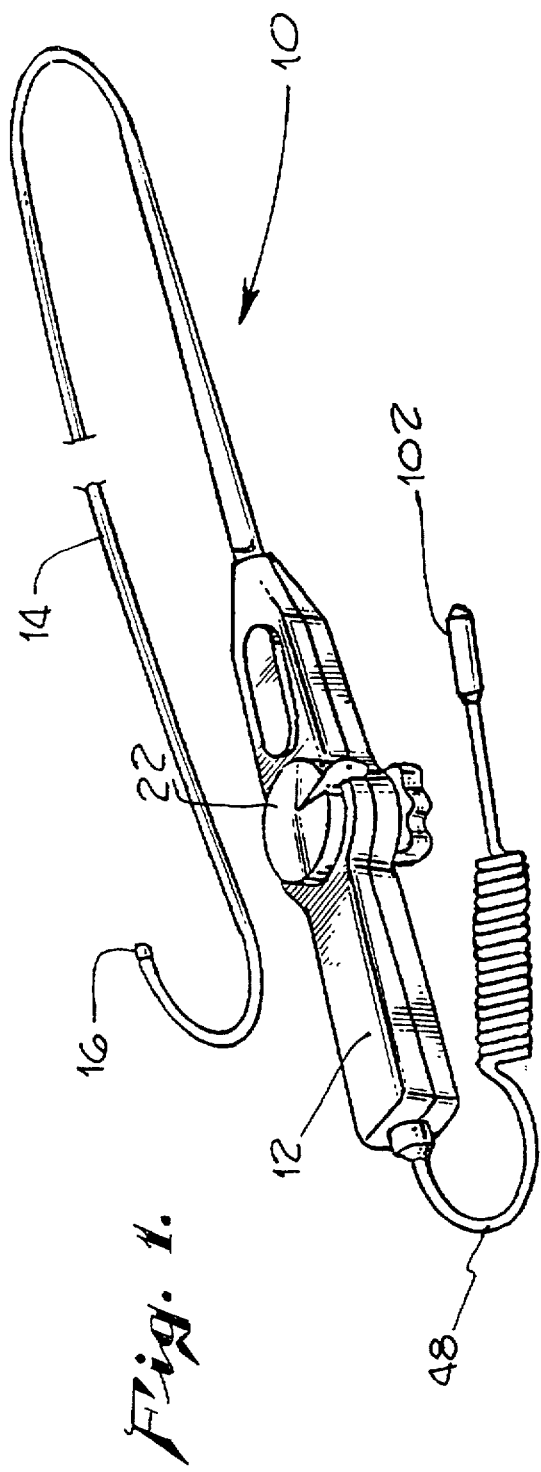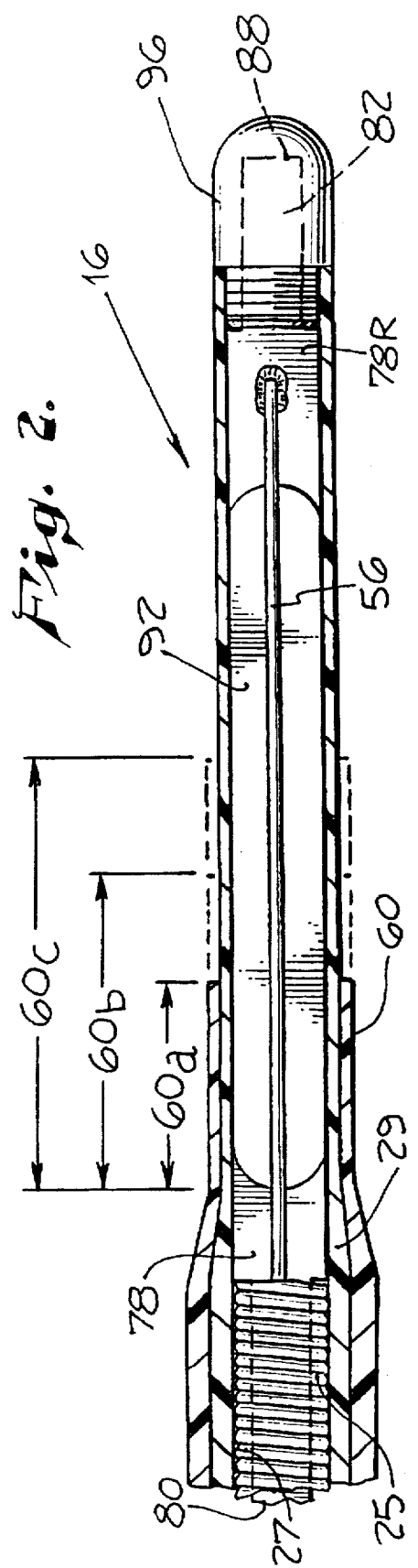

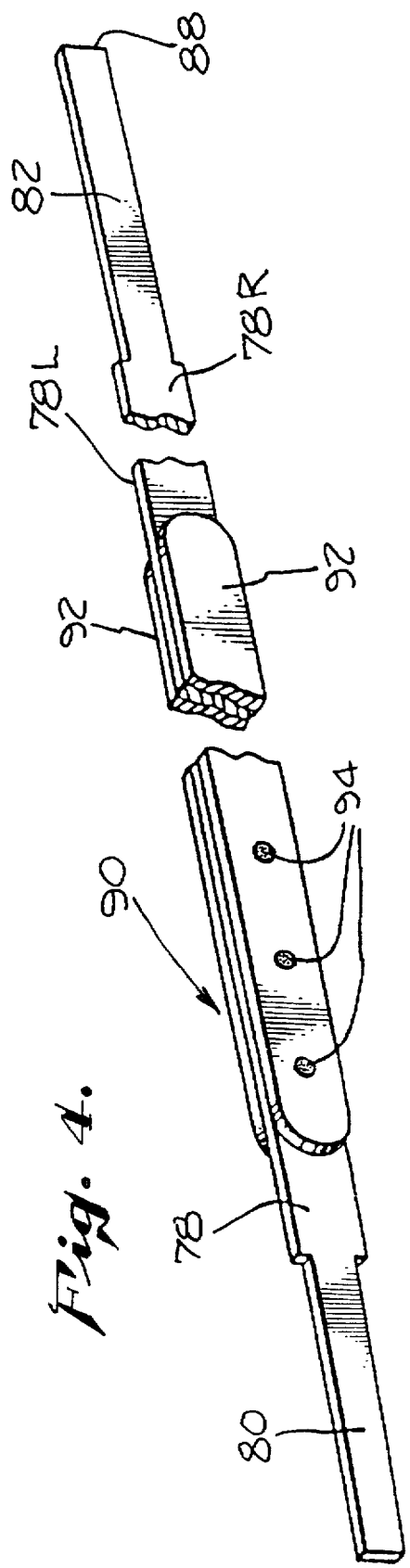
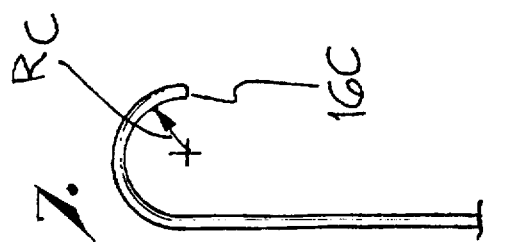
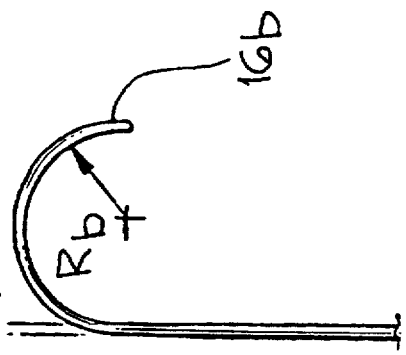
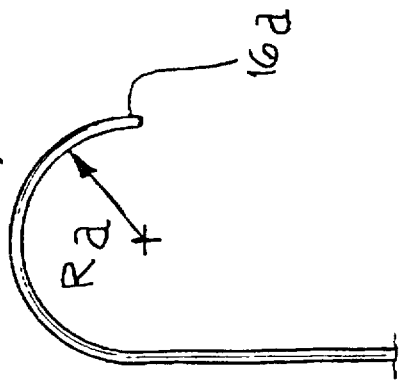

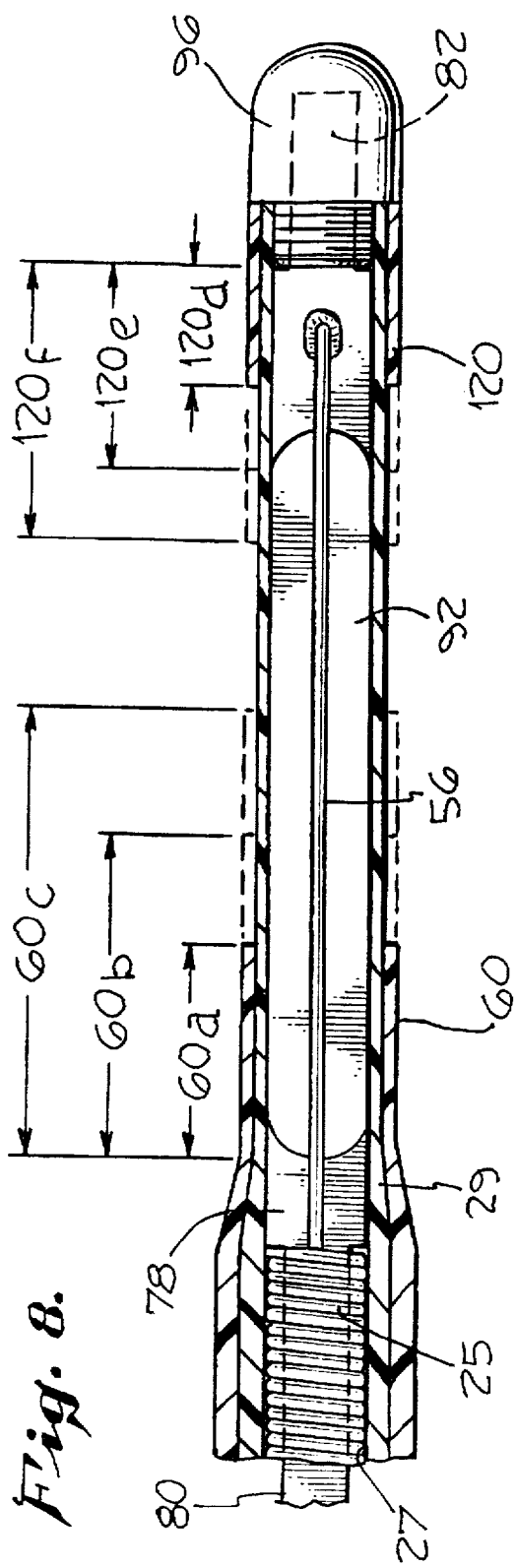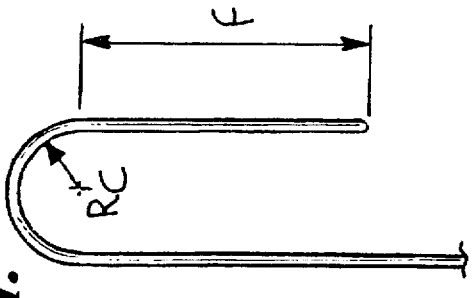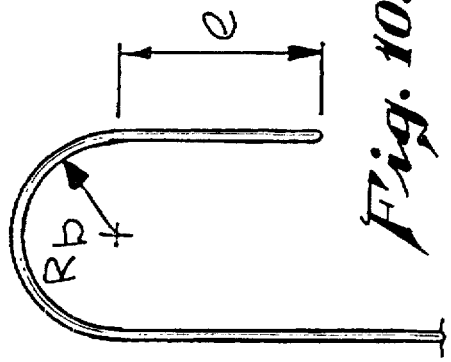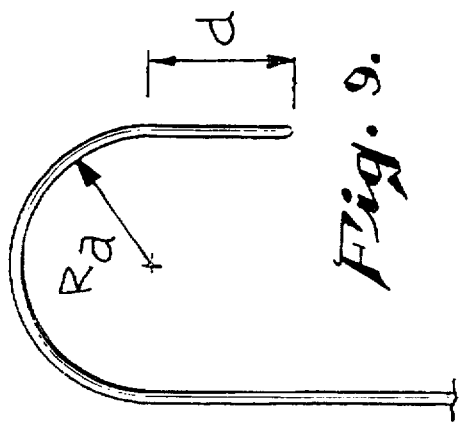

1

STEERABLE ELECTROPHYSIOLOGY CATHETER

FIELD OF THE INVENTION

This invention relates to catheters and, particularly, to controlling the bending characteristics thereof. More particularly, the invention relates to such catheters which can be steered or laterally deflected into curve configurations that are preselected in accordance with the invention.

BACKGROUND OF THE INVENTION

Cardiac mapping is used to locate aberrant electrical pathways and currents emanating within the heart. Such aberrant pathways cause irregular contractions of the heart muscle resulting in life-threatening patterns or disrhythmias.

Ablation of cardiac tissue to create lesions within the heart in order to eliminate the aberrant pathways is desired, as is the formation of lesions for treatment of various disorders such as atrial fibrillation. Various steering mechanisms for catheters carrying electrodes for such purposes have heretofore been developed and used.

To provide catheters having different characteristics to access various endocardial sites, physicians have a use number of different catheters, each of which provides a different characteristic. The use of multiple separate catheters having differing steering characteristics increases the risk inherent in these difficult procedures. A need has thus existed for catheters which, in the nonlinear environment found within the heart, are capable of being steered in order to place ablation elements at a number of desired locations while creating intimate tissue contact by each active ablation element.

Particularly, a need has existed for the ability to provide catheters which could effectively and accurately be steered into selected curves having, for example, greater or lesser degrees of curvature. Other types of curve configurations which are desired may include curves formed at a preselected desired location along the length of the distal section of the catheter with straight sections of various selected lengths located distally of the curves.

SUMMARY OF THE INVENTION

The present invention provides catheters, usable in both diagnostic and therapeutic applications, that enable a physician to swiftly and accurately steer the distal end of each catheter into a selected curved shape within the body of a patient. A catheter that embodies the invention allows physicians to better steer the catheter to access various endocardium sites using a catheter constructed to bend accurately into a preselected curved shape.

In its broadest aspect, the invention provides a means of predictably producing a catheter having a desired bend location and curve shape when steered by manipulation of external controls. Thus the ease and reliability of accessing, measuring electrical activity and ablating cardiac tissue in the heart are increased.

Briefly, the invention provides a catheter for percutaneous insertion into a living body having a steering mechanism that preferably includes a steering member such as flattened (usually a leaf spring)or cantilevered spring, bendable in response to external forces to steer the catheter tip. The catheter distal tip is preferably provided with an operative component such as a tip electrode. At least one steering wire (and preferably two) is attached to the steering member for transmitting bending force thereto from a remote control mechanism. A steerable catheter includes a handle, an elongated catheter body, a steering tube preferably formed by an elongated coiled spring. The steering tube has a distal end that terminates short of the distal end of the catheter, and a steering member spring having a bendable portion extending outside of the distal end of the steering tube for bending the distal end of the catheter in response to an applied force exerted by one or more steering wires. A controller is positioned on the handle and attached to the steering wire, for applying tension to the steering wire. At least one and preferably two or more sleeves of polymeric material are formed around a part, but less than the entire length of the distal portion of the catheter which extends distally from the steering tube. The sleeves may be secured around the distal portion by heat shrinking. The bending characteristics of the catheter are modified by the length and thickness of the sleeves as well as the physical characteristics of the polymer used. The preferred polymeric materials have a high burst strength and a high tensile modulus, with a very thin wall thickness and which reach their ultimate strength with minimal strain measurement, preferably 1% strain or less. An preferred example of a suitable material is a polyester such as polyethylene terephthalate.

Further, objects and advantages of the invention will become apparent from the following detailed description and accompanying drawings.

BRIEF DESCRIPTION OF DRAWINGS

FIG. 1 a perspective view of a catheter and catheter handle assembly in accordance with the invention;

FIG. 2 is a cross-sectional view of the tip portion of the catheter shown in FIG. 1 shown on a greatly enlarged scale and showing a sleeve on a proximal portion thereof;

FIG. 4 is a perspective view of the stiffening assembly for the support wire of the catheter;

FIGS. 5–7 are fragmentary views of distal portions of catheters according to various modifications of the structure shown in FIG. 2;

FIG. 8 is a cross-sectional view of the tip portion of a further embodiment of the catheter shown in FIG. 1 shown on a greatly enlarged scale; and, FIGS. 9–11 are fragmentary views of distal portions of catheters according to various modifications of the structure shown in FIG. 8.

DETAILED DESCRIPTION OF PREFERRED EMBODIMENTS

Figure 3:
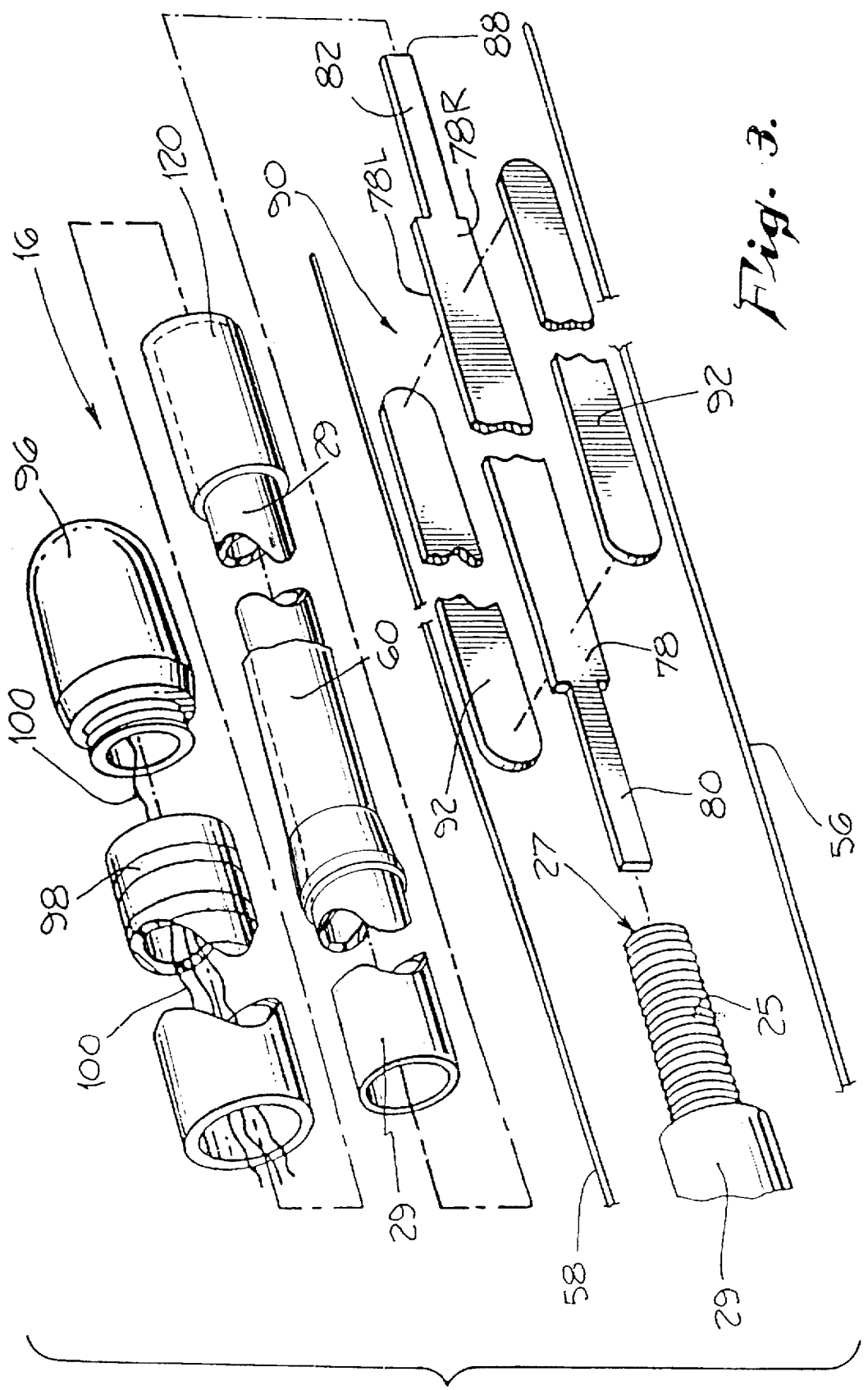
FIG. 3 is a fragmentary exploded disassembled view perspective of the electrode tip assembly of the catheter.

FIG. 1 shows a steerable catheter 10 that embodies the features of the invention. The catheter 10 includes several main parts: a handle 12, a catheter tube or body 14, and a steerable distal tip assembly 16. In use, the catheter 10 enables electrophysiology diagnosis or therapy in the interior regions of the heart.

When used for this purpose, a physician grips the handle 12 and maneuvers the catheter body 14 through a main vein or artery (which is typically the femoral vein) into the interior region of the heart that is to be treated. The physician then further steers the distal tip assembly 16 to place it in contact with the tissue that is to be monitored or ablated. For ablation, the physician directs energy to an electrode in the assembly 16 to ablate the tissue contacted.

The handle 12 encloses a steering mechanism which may be, for example, in the form of a rotating cam wheel of the type shown in U.S. Pat. No. 5,195,968, the disclosure of which is incorporated herein by reference. It will be understood that many other mechanisms that allow for selective pulling of the steering wires in the catheter can be substituted.

The steering wires 56 and 58 extend from handle 12 through the length of the interior of catheter body 14 and are attached to a steering wire or spring 78 in the electrode tip assembly 16.

The catheter body 14 is a flexible shaft attached to the handle 12. While it can be variously constructed, in a preferred embodiment, the catheter body 14 is a length of stainless steel coiled into a flexible spring 25 enclosing an interior bore 27 which in turn is enclosed in a braided sheath 29 of plastic material. The steering wires 56 and 58 preferably pass through the interior bore 27, which leads to the distal tip assembly 16 where the steering wire are attached to a bendable main support wire 78. In the illustrated embodiment, the main support wire 78 is made of stainless steel flat wire stock in an elongated shape about 0.035 inch wide and about 0.005 inch thick. The main support wire 78 is preferably about 3 inches in total length.

In the distal end of the catheter body 14 there is no surrounding coil or shield, around the steering assembly. Positioned in the distal end region and overlying a portion of the distal end of coil 25 is a curve adjusting sleeve 60.

The shaft 25 may constructed in various ways. In the embodiment shown in FIG. 3, the shaft 25 comprises a length of stainless steel coiled into a flexible spring enclosing the interior bore 27. A braided sheath 29 of plastic material encloses the coil.

The electrode tip assembly 16 includes a bendable main support wire 78 having left and right faces 78L and 78R. In one example of the illustrated embodiment, the main support wire 78 is made of stainless steel flat wire stock in an elongated shape about 0.035 inch wide and about 0.005 inch thick. The main support wire 78 is about 3 inches in total length.

The opposite ends of the main support wire 78 are cut away to form stepped shoulders 80 and 82. In the illustrated embodiment, the shoulders 80 and 82 are about 0.024 inch wide and aligned along the centerline of the main support wire 78. Each shoulder 80 and 82 is about 0.12 inch in length.

As FIG. 3 shows, one stepped shoulder 80 fits within the distal end of the flexible guide tube shaft 25 to append the electrode tip assembly 16 to the guide tube assembly 14. When properly oriented, the left and right faces 78L and 78R of the main support wire 78 lie in a plane that is generally parallel to the axis about which the cam wheel 22 rotates. Stated differently, when the user holds the handle assembly 12 in a horizontal plane, the left and right faces 78L and 78R of the main support wire 78 lie in a vertical plane.

As FIG. 3 also shows, the distal end of the left steering wire 58 is soldered to the left face 78L of the main support wire 78. Pulling of the left steering wire 58 bends the main support wire 78 to the left.

Also, the distal end of the right steering wire 56 is soldered to the right face 78R of the main support wire 78. When pulled by right steering wire 56 the main support wire 78 bends to the right.

In the illustrated embodiment shown in FIG. 4, a stiffening spring assembly 90 stiffens the center support near the distal end of the guide tube shaft 25. The stiffening spring assembly 90 includes two leaf springs 92 that sandwich the main support wire 78 between them. Each leaf spring 92 is made of stainless steel flat wire stock in an elongated shape that is, in a preferred embodiment, about 0.039 inch wide and about 0.0029 inch thick.

The stiffening spring assembly 90 can sized and configured to provide the degrees of stiffness and variance wanted. In the illustrated embodiment, the stiffening spring assembly 90 stiffens the main support wire 78 beginning about 0.03 to 0.05 inch from the inner edge of the attachment shoulder 80 and extending from there about 1.5 inches.

In the illustrated embodiment, spot welds 94 secure the leaf springs 92 to the main support wire 78. The three spot welds 94 shown are clustered near the proximal end of the stiffening spring assembly 90. There, they are evenly spaced, with the most distal spot weld 94 being about 0.10 inch from the proximal end of the stiffening spring assembly 90.

In the illustrated embodiment, the distal end of the electrode tip assembly 16 carries an ablation tip electrode 96 and several ring electrodes 98. Interior conducting wires 100 are connected to the tip electrode 96 and the ring electrodes 98. The conducting wires 100 extend along the main support wire 78, through the interior bore of the guide tube shaft 25, and into the handle housing 12 to join a coaxial cable 48 that extends from the rear of the housing 12.

The coaxial cable 48 ends with plugs 102. The plugs 102 connect with appropriate conventional catheter control equipment (not shown). The conducting wires 100 transfer electrical current from the ring electrodes 98 indicative of electrical activity within the heart as well as ablation energy to electrode 96.

In accordance with the invention the curvature characteristics of a number of catheters otherwise having similar steering characteristics can be modified and selected by use of different selectively interchangeable polymeric sleeves. Referring to FIG. 2, the sleeves 60 can be provided in differing lengths to result in curves having differing radii. Relating FIG. 2 with FIGS. 5–7, a shorter sleeve having a segment 60a extending distally from the proximal end of leaf spring 92, of a length 60a, is associated with a relatively large curve shown in FIG. 5 and identified as $R_a$. Similarly, sleeve 60b has a incrementally greater length than sleeve 60a. Sleeve 60b, when installed within the end of a catheter 16b, is associated with a somewhat tighter curvature $R_b$ as seen in FIG. 6. Sleeve 60c has an even greater length than sleeve 60b. Sleeve 60c, when installed within catheter tip 16c, as illustrated in FIG. 7, is associated with providing a catheter distal tip section which forms an even tighter radius $R_c$.

In the alternate embodiment of FIG. 8, a second sleeve 120 is provided near the distal end of the steering mechanism of catheter distal tip 16.

While various preferred embodiments of the invention have been shown for purposes of illustration, it will be understood that those skilled in the art may make modifications thereof without departing from the true scope of the invention as set forth in the appended claims including equivalents thereof.

What is claimed is:

1. A catheter steering mechanism comprising:
   a tubular catheter body containing a steering tube having proximal and distal ends;
   a lumen extending through the length of the steering tube and having a distal end that terminates short of the distal end of the catheter body.
   a steering spring having an axis and a bendable portion of substantially uniform cross section extending distally for a selected axial length beyond the distal end of said steering tube.

at least one steering wire extending through the lumen, having a first end attached to the steering spring at a first location outside the distal end of the lumen and having a second end extending through the proximal end of said lumen;

a controller positioned at the proximal end of said catheter and attached to said steering wire for applying tension thereon to bend the distal end of the steering spring toward the tense steering wire, a flexible tubular body enclosing said steering tube and having a distal section enclosing said steering spring and forming a distal portion of said catheter body, and, a first sleeve of high burst strength polymeric material formed around a portion of said flexible tubular body, at least a portion of the axial length of said bendable portion of said steering spring and at least a portion of said steering tube, whereby the bending characteristics of said distal portion are modified due to said sleeve.

2. The steering mechanism of claim 1, wherein a second sleeve of polymeric material is formed around a part of said flexible tubular body longitudinally offset and separated in a distal direction from said first flexible tubular body.

3. The steering mechanism of claim 1, wherein said controller includes:

a housing connected to said steering tube within which a steering control mechanism for applying tension to said steering wires is housed.

4. The steering mechanism of claim 3, wherein said sleeves comprise a polyester polymer.

5. The steering mechanism of claim 4 wherein said polymer comprises polyethylene terephthalate.

6. A steerable catheter including a handle, an elongated catheter body, a steering tube formed by an elongated coiled spring having a proximal end attached to the handle and a distal end and a lumen therethrough, the steering tube having a distal end that terminates short of the distal end of the catheter;

a steering spring having an axis and a bendable portion extending outside the distal end of said lumen for bending the distal end of the catheter in response to an applied force;

a first steering wire extending through the lumen, having a first end attached to the steering spring at a first location outside the distal end of the lumen and having a second end exiting the proximal end;

a controller positioned on the handle and attached to the wire, for placing tension thereon at least one of the first steering wire and the second steering wire, for applying force to the steering wire to bend the distal end of the steering tube toward the tensed steering wire, and, a first sleeve of polymeric material formed around a part, but not all of the length of said catheter, the first sleeve extending distally from the elongated coiled spring and defining a proximal portion located between the proximal and distal ends of the coiled spring, whereby the bending characteristics of said catheter are modified.

7. A catheter according to claim 6 wherein the polymeric material comprises a polyester polymer.

8. A catheter according to claim 6 wherein said polymeric material comprises polyethylene terephthalate.

9. A catheter according to claim 6 wherein two formed polymeric sleeves longitudinally offset and spaced from each other encompass the length of said catheter which extends distally from the elongated coiled spring, whereby the bending characteristics of said catheter are modified.

10. A catheter steering mechanism comprising:

a tubular catheter body containing a steering tube having proximal and distal ends;

a lumen extending through the length of the steering tube and having a distal end that terminates short of the distal end of the catheter body, a steering spring having an axis and a bendable portion of substantially uniform cross section extending distally for a selected axial length beyond the distal end of said steering tube, at least one steering wire extending through the lumen, having a first end attached to the steering spring at a first location outside the distal end of the lumen and having a second end extending through the proximal end of said lumen;

a controller positioned at the proximal end of said catheter and attached to said steering wire for applying tension thereon to bend the distal end of the steering spring toward the tensed steering wire, a flexible tubular body having a distal section enclosing said steering spring and forming a distal portion of said catheter body, and, a plurality of selectively interchangeable polymeric sleeves of high burst strength, each having a different preselected length or thickness, a selected one of said sleeves being heat shrunk around at least a portion of the axial length of said bendable spring, whereby selected curvature characteristics on bending of said distal portion are imparted to said catheter.

11. A catheter tip assembly, comprising:

a steering tube defining a distal end and a proximal end;

a tip member;

a steering spring extending from the steering tube to the tip member, the steering spring including a bendable portion outside the steering tube;

a sheath covering the steering spring and at least a portion of the steering tube, the sheath defining a distal end abutting the tip member; and a sleeve, defining a distal end and a proximal end, formed around a portion of the sheath such that the distal end of the sleeve is in spaced relation to the tip member, the sleeve covering at least a portion of the bendable portion of the steering spring.

12. A catheter tip assembly as claimed in claim 11, wherein the tip member comprises an electrode.

13. A catheter tip assembly as claimed in claim 11, wherein the steering tube defines a lumen and the steering spring comprises a shoulder extending into the lumen.

14. A catheter tip assembly as claimed in claim 11, wherein the steering tube comprises a coil spring.

15. A catheter tip assembly as claimed in claim 11, wherein the sleeve covers at least a portion of the steering tube.

16. A catheter tip assembly as claimed in claim 11, wherein the sleeve defines a first sleeve and the portion of the sheath defines a first portion, the catheter tip assembly further comprising:

a second sleeve defining a distal end and a proximal end, the second sleeve being formed around a second portion of the sheath such that the proximal end of the second sleeve is in spaced relation to the distal end of the first sleeve and a third portion of the sheath between the first and second portions is not covered by the first and second sleeves.

17. A catheter tip assembly as claimed in claim 16, wherein the distal end of the second sleeve abuts the tip member.

18. A catheter tip assembly, comprising:

a steering tube defining a distal end and a proximal end;

a steering spring extending from the steering tube, the steering spring defining a distal end and including a bendable portion outside the steering tube;

a sheath covering at least the bendable portion of the steering spring and at least a portion of the steering tube, the sheath defining a distal end located substantially adjacent to the distal end of the steering spring; and a sleeve, defining a distal end and a proximal end, formed around a portion of the sheath such that the distal end of the sleeve is in spaced relation to the distal end of the sheath, the sleeve covering at least a portion of the bendable portion of the steering spring.

19. A catheter tip assembly as claimed in claim 17, wherein the steering tube defines a lumen and the steering spring comprises a shoulder extending into the lumen.

20. A catheter tip assembly as claimed in claim 17, wherein the steering tube comprises a coil spring.

21. A catheter tip assembly as claimed in claim 17, wherein the sleeve covers at least a portion of the steering tube.

22. A catheter tip assembly as claimed in claim 17, wherein the sleeve defines a first sleeve and the portion of the sheath defines a first portion, the catheter tip assembly further comprising:

a second sleeve defining a distal end and a proximal end, the second sleeve being formed around a second portion of the sheath such that the proximal end of the second sleeve is in spaced relation to the distal end of the first sleeve and a third portion of the sheath between the first and second portions is not covered by the first and second sleeves.

23. A catheter tip assembly as claimed in claim 22, wherein the distal end of the second sleeve is substantially aligned with the distal end of the sheath.

24. A catheter tip assembly kit, comprising:

a steering tube defining a distal end and a proximal end;

a steering spring extending from the steering tube, the steering spring defining a distal end and including a bendable portion outside the steering tube;

a sheath covering at least the bendable portion of the steering spring and at least a portion of the steering tube, the sheath defining a distal end located substantially adjacent to the distal end of the steering spring;

a first interchangeable sleeve, defining a distal end and a proximal end, adapted to be formed around a portion of the sheath such that the distal end of the first interchangeable sleeve is in spaced relation to the distal end of the sheath and the first interchangeable sleeve covers at least a portion of the bendable portion of the steering spring, the first interchangeable sleeve defining a first bending characteristic; and a second interchangeable sleeve, defining a distal end and a proximal end, adapted to be formed around a portion of the sheath such that the distal end of the second interchangeable sleeve is in spaced relation to the distal end of the sheath and the second interchangeable sleeve covers at least a portion of the bendable portion of the steering spring, the second interchangeable sleeve defining a second bending characteristic.

25. A kit as claimed in claim 24, wherein the first bending characteristic comprises a first length, the second bending characteristic comprises a second length, and the first length is greater than the second length.

26. A kit as claimed in claim 24, wherein the first bending characteristic comprises a first thickness, the second bending characteristic comprises a second thickness, and the first thickness is greater than the second thickness.

* * * * *